United States Patent
Muench

[19]

[11] Patent Number: 5,880,352
[45] Date of Patent: Mar. 9, 1999

[54] METHOD AND DEVICE FOR DETERMINING THE CONCENTRATION OF A SUBSTANCE IN A GASEOUS MEDIUM

[75] Inventor: Reinhold Muench, Freiburg, Germany

[73] Assignee: Testo GmbH & Co., Lenzkirch, Germany

[21] Appl. No.: 960,281

[22] Filed: Oct. 29, 1997

[30] Foreign Application Priority Data

Oct. 31, 1996 [DE] Germany .................. 196 43 981.7

[51] Int. Cl.⁶ ............................................. G01N 27/416
[52] U.S. Cl. ............................................................ 73/23.2
[58] Field of Search .................... 73/23.2, 23.31, 73/23.32, 863.03

[56] References Cited

U.S. PATENT DOCUMENTS

| | | |
|---|---|---|
| 3,923,461 | 12/1975 | Barden . |
| 4,565,086 | 1/1986 | Orr, Jr. . |
| 5,569,838 | 10/1996 | Broedel et al. ................ 73/23.31 |
| 5,691,464 | 11/1997 | Cao ............................... 73/23.31 |
| 5,756,360 | 5/1998 | Harvey et al. ................ 73/23.31 |

FOREIGN PATENT DOCUMENTS

| | | |
|---|---|---|
| 31 35 455 A1 | 9/1981 | Germany . |
| 43 34 336 A1 | 10/1993 | Germany . |
| 44 07 345 A1 | 3/1994 | Germany . |
| 55-022377 | 2/1980 | Japan . |

*Primary Examiner*—Robert Raevis
*Attorney, Agent, or Firm*—Foley, Hoag & Eliot LLP

[57] ABSTRACT

A method for determining the concentration of a substance in a gaseous medium using a chemical sensor is disclosed. To ensure that the concentration is within the nominal measuring range of the sensor, the sample gas stream is mixed with a diluting gas stream in a mixing device to form a measured gas stream. This mixing process involves setting an adjustable dilution ratio and alternately supplying the sample gas stream and diluting gas stream to the mixing device. By adjusting the amount of time each gas is supplied to the mixing device the dilution ration can be varied to thereby maintain the concentration of the substance detected by chemical sensor within the nominal measuring range of the sensor. Calculation of the concentration of the substance is thus simplified since the dilution ration is automatically a known quantity since the sample gas stream and diluting gas stream are supplied cyclically alternately and in succession with a definite volume flow to measuring device.

15 Claims, 2 Drawing Sheets

METHOD AND DEVICE FOR DETERMINING THE CONCENTRATION OF A SUBSTANCE IN A GASEOUS MEDIUM

BACKGROUND OF THE INVENTION

1. Field of the Invention

This invention relates to a method for determining the concentration of a substance, and more particularly relates to a method for determining the concentration of a substance in a gaseous medium with a chemical sensor that has a nominal measuring range for the concentration of the substance.

2. Description of the Related Art

Chemical or electrochemical sensors for determining the concentration of substances in gaseous media have a nominal measuring range in which measurement is possible with a certain accuracy. If measurement is attempted outside of this range the sensor will operate inaccurately. If extreme deviations from the nominal measuring range are encountered, the sensor may also be damaged.

Sensors of this type are therefore suitable for such concentration measurements in gaseous media only when the anticipated concentration of the substance to be measured is expected to fall within the nominal measuring range. For a number of applications the nominal measuring range of the sensor makes it impossible to directly measure the concentration of the gaseous media since at least a portion of the anticipated concentration values exceeds that of the nominal measuring range of the sensor.

One known way to overcome this problem is to feed a measured dilution gas stream to the chemical sensor to thereby dilute the concentration of the substance in question to within the nominal measuring range of the sensor. Thus the actual value of the concentration of the substance in the gaseous medium can be determined by calculation from the meter reading using the dilution factor.

Specifically, therefore, a sample gas stream is first removed from the gaseous medium and mixed in a mixing device with a diluting gas stream, especially a stream of air obtained from the environment, to form a measured gas stream. The dilution ratio can be modified by varying the amounts of sample gas stream and diluting gas stream. The measured gas stream thus obtained is fed to the chemical sensor, which generates a detection signal as a measure of the concentration of the substance. As soon as the detected concentration falls outside the nominal measuring range, the concentration in the sample gas stream is corrected by adjusting the dilution ratio. The concentration of the substance in the gaseous medium is then calculated by evaluating the detection signal, taking the dilution ratio into account.

In this connection, knowledge, as exact as possible, of the dilution ratio takes on particular significance, since it directly determines the accuracy of the measurement result. For this purpose, the concentration of an (additional) substance component is measured before and after dilution and the dilution ratio is determined from this. This requires that this (additional) substance component be known and constant in one of the two positions, in other words before or after mixing. One possible solution referred to as being preferable consists in using an air-gas mixture as the diluting gas stream that is drawn from the environment. For example, oxygen can be used as a substance component that is known and is available in constant quantity before mixing with the sample gas stream. The dilution ratio can be determined reliably from the ratios of the oxygen concentration before and after mixing.

One disadvantage to this solution is that it is a relatively expensive way to determine the dilution ratio because it is necessary to provide an additional sensor, especially to evaluate its detection signal. The software expense involved is also not inconsiderable, especially when the dilution ratio must be adjusted in the event of dynamic processes, for example fluctuations in the concentration of the substance to be measured.

Accordingly, it would be advantageous to improve a method and a device for determining the concentration of a substance in a gaseous medium which can achieve high accuracy at a comparatively low cost. In particular, the nominal measuring range of the chemical sensor, even with concentration values of the substance of the gaseous medium that fall outside this nominal range, must be maintained with the simplest possible design means and with the lowest possible software expense.

SUMMARY OF THE INVENTION

This and other objects of this invention are achieved by supplying the sample gas stream and the diluting gas stream to a mixing chamber or sensor alternately and sequentially in cycles and calculating the dilution ratio from the cycle ratio. A prerequisite for this is that the sample gas stream and diluting gas stream must each be delivered at a specific volume flowrate. The advantage consists in the fact that no special sensor is required to determine the dilution ratio. The cycle ratio can be determined easily from the quotient of the time components that elapse for supplying the sample gas stream and the diluting gas stream. Time measurement as such is trivial and as a rule can be performed using a timer module controlled by a microprocessor unit.

The calculation of the dilution ratio can be structured especially simply if the volume flows of the sample gas stream and diluting gas stream have the same value. In this case, the cycle ratio already corresponds directly to the dilution ratio. The calculation and software expense is extremely low in this case.

Advantageously, the sample gas stream and the diluting gas stream are supplied through a mixing valve, with an especially simple design being made possible by using a 3/2-way valve, which releases the sample gas stream and the volume gas stream alternately by sliding back and forth. The control device in this case merely requires a switching pulse to be applied cyclically to adjust the desired dilution ratio. It is also possible to use 2/2-way valves connected in parallel instead of the 3/2-way valve.

The mixing valve is preferably actuated by a central control device that evaluates the detection signal of the chemical sensor and determines the required cycle ratio directly from it, which is required to maintain the nominal measuring range. Thus, the concentration of the substance in a gaseous medium can be determined rapidly.

Basically, the method according to the invention can also be designed as a dynamic measurement method in which the dilution ratio is adjusted continuously. Fluctuations in the concentration of the substance to be determined are compensated by continuous adjustment of the dilution ratio so that the measured gas stream always has a concentration in the nominal measuring range of the chemical sensor.

In extreme cases, it is possible to keep the concentration in the measured gas stream practically constant and hence at the optimum measured value of the sensor, so that the cycle ratio is directly proportional to the output concentration of the substance in the gaseous medium. The accuracy of the measurement result thus depends primarily on the accuracy of the time measurement, which in practice poses no problems whatever.

The use of an air stream as the diluting gas stream has proven especially advantageous. As a rule, the air can be drawn directly from the environment and possibly conducted through an air filter directly to the mixing device.

It is also possible to use other gas streams as diluting gas streams, such as from tanks. Nitrogen has proven to be especially suitable. By using suitable measures, for example a pump with a bypass or a pressure regulator with a bypass, assurance must be provided that the diluting gas stream is supplied to the mixing valve at zero pressure.

One aspect of this invention provides a plurality of chemical sensors for detecting a plurality of substances in the gaseous medium. The dilution ratio in this case is adjusted as a function of the detection signal of the chemical sensor whose reading is determined at the outset to be furthest from the nominal measuring range when measurement begins. This ensures that the chemical sensor at the greatest risk is reliably protected.

Preferably, on the basis of the detection signal from one or more previous measurements, the anticipated detection signal of the next measurement can be determined and the dilution ratio can then be adjusted by gradient formation. As a result of this preliminary estimate of the anticipated detection signal, a faster adjustment can be made so that the measured value falls within the nominal measuring range. In many cases, subsequent regulation can be eliminated since the current detection signal already correlates with the nominal measuring range of the sensor.

During continuous measurement, the dilution ratio can be changed stepwise whenever the nominal measuring range is exceeded. On the other hand, it is possible to perform a continuous quasi-stepless change in the dilution ratio so that the measured value can be kept within a relatively narrow interval of the nominal measuring range or at the optimum measured value.

The method according to one aspect of this invention for dynamic dilution of a sample stream carried by a gaseous medium to maintain the nominal measuring range of chemical sensors uses electrical detection signals from these sensors to determine whether a nominal measuring range is being maintained. If the detection signal falls outside the nominal measuring range (as a partial range of a total measuring range), the dilution ratio is changed. The dilution ratio is then implemented by cyclic, alternate, and successive supply of a sample gas stream and a diluting gas stream.

A device suitable for working the method preferably includes a device for collecting the sample gas stream; a diluting device for diluting the sample gas stream with a diluting gas stream, with the sample gas stream and the diluting gas stream being supplied alternately and cyclically to a mixing device through a mixing valve and being mixed to form a measured gas stream; at least one chemical sensor for generating a detection signal as a measure of the concentration of the substance in the measured gas stream; and a control device which, depending on the value of the detected concentration, adjusts the dilution ratio by setting the cycle such that the concentration of the substance in the measured gas stream is kept in the nominal measuring range of the chemical sensor. In this manner, it is possible to construct a device which has a structurally simple design and which also enables an extremely easy way to set or adjust the dilution ratio.

Advantageously, the mixing device is in the form of a mixing chamber with integral turbulence generators to ensure homogenous mixing that is intensive as possible of the sample gas stream and the diluting gas stream. This is especially important in conjunction with this invention since the partial gas streams are supplied alternately to the mixing chamber. Nozzles, capillaries, or so-called static mixers for example are suitable as turbulence generators, which create strong turbulence for intimate mixing in relatively small volumes.

Preferably, a bypass is provided for bypassing the diluting device, through which bypass the sample gas stream that is drawn in is fed directly to the chemical sensors. A design of this kind is especially valuable when the anticipated concentration allows the chemical sensors to be operated in the nominal measuring range and dilution is only required in individual cases when the measured value is exceeded.

Advantageously, a prechamber can be connected directly upstream of the mixing valve to serve as a sort of buffer, and can compensate for fluctuations in the feed range of the sample gas stream.

Finally, a delivery pump for the measured gas stream is advantageous when the mixing chamber is connected downstream. Depending on the position of the mixing valve at the moment, the valve delivers either sample gas or diluting gas. The arrangement selected downstream from the mixing chamber ensures that the measured gas stream is drawn in by the pump and fed to the sensors with uniform, thorough mixing.

BRIEF DESCRIPTION OF THE DRAWINGS

The preferred embodiments of the present invention will now be described more specifically with reference to the attached drawings, wherein.

DETAILED DESCRIPTION OF THE PREFERRED EMBODIMENTS

Figure 1:
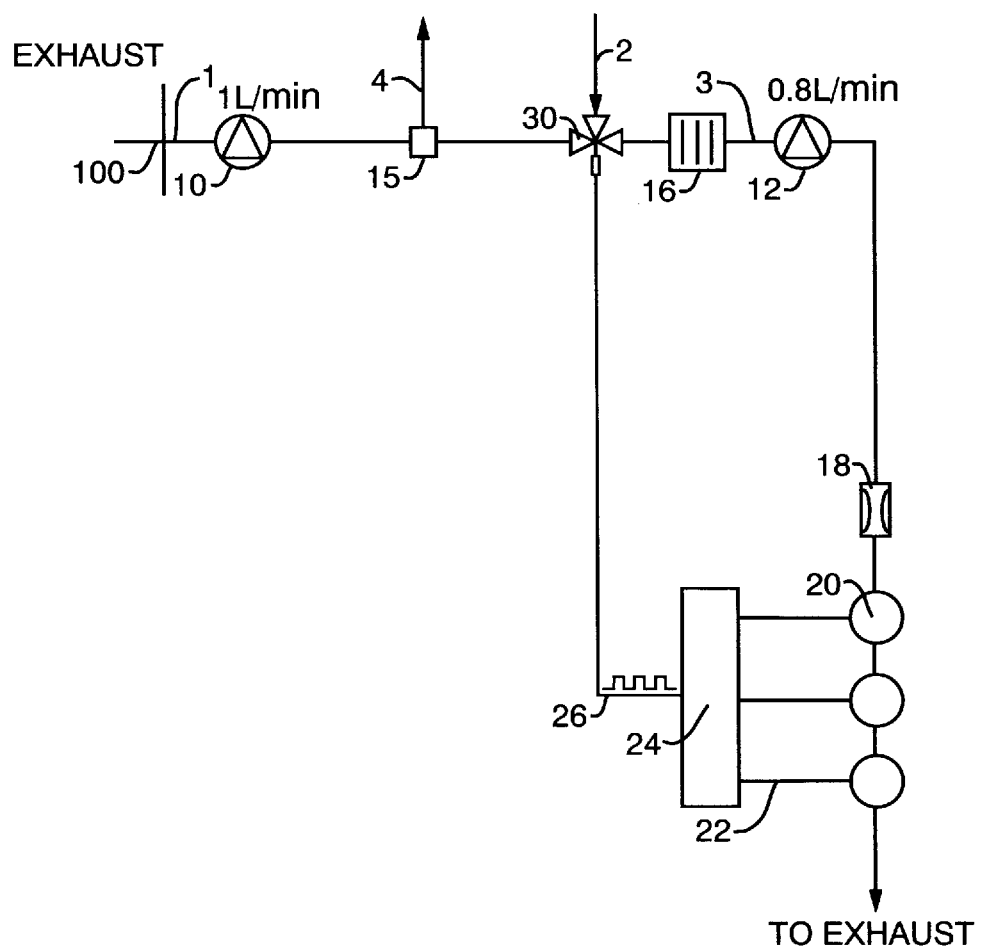
FIG. 1 is a schematic diagram showing the working of the method.

The basic working of the method is evident from FIG. 1. A gaseous medium 100 to be examined, for example the exhaust from a furnace, is to be investigated to determine the content (concentration) of certain substances. Sensors 20 are provided for the purpose, whose detection signals 22 are fed to a central control device 24 in which they are evaluated and displayed, stored, or processed further for example. Chemical sensors 20 each have a specific nominal measuring range for the concentration of the substance to be investigated, said range correlating with a nominal value range of detection signal 22.

A sample gas stream 1 is drawn off from gaseous medium 100. A delivery pump 10 is provided for this purpose, said pump delivering sample gas stream 1 continuously and with a specific volume flow that is always constant under all operating conditions. Sample gas stream 1 is fed through a mixing valve 30 to a mixing chamber 16. Mixing valve 30 is a pulsed 3/2-way valve operated by control device 24 using a control signal 26.

A diluting gas stream 2 is supplied to mixing chamber 16 through mixing valve 30, in which chamber intensive mixing with sample gas stream 1 to form a measured gas stream 3 is performed by turbulence generators, not shown here in greater detail. Measured gas stream 3 is delivered by delivery pump 12 with a defined and constant volume flow through a capillary 18 to chemical sensors 20. Chemical sensors 20 pick up the concentration of the substances in question in the diluted measured gas stream 3. The output from the sensors is used in conjunction with the dilution ratio to calculate the true concentration in the gaseous medium 100.

Mixing valve 30 shifts cyclically and alternately back and forth between sample gas stream 1 and diluting gas stream 2 so that the line section (not shown here in greater detail) between mixing valve 30 and mixing chamber 16 contains successive partial volumes ("packets") of sample gas stream 1 and diluting gas stream 2. Since mixing valve 30 has only two switching states, either the path for sample gas stream 1 or the one for diluting gas stream 2 is open. As long as mixing valve 30 opens the way for sample gas stream 1, the path for diluting gas 2 is closed. When mixing valve 30 is switched, the path is closed for sample gas stream 1 and the one for diluting gas stream 2 is simultaneously opened. Diluting gas stream 2 results from the fact that delivery pump 12 draws air from the environment through mixing chamber 16 and mixing valve 30.

Since delivery pump 10 continues to supply sample gas during this switching activity, there is a branch 14 upstream of mixing valve 10 as viewed in the flow direction, through which branch sample gas stream 1 is recycled as a bypass stream 4 to gaseous medium 100 in the outflow area (exhaust) for example. In this case, the volume flow of sample gas stream 1 corresponds to the volume flow of bypass flow 4.

As soon as mixing valve 30 again opens the line for sample gas stream 1, the sample gas stream is fed to mixing chamber 16, with a volume flow that is specified by delivery pump 12. Since this volume flow is less than the sample gas stream 1 supplied through delivery pump 10, a portion of the sample gas escapes in the form of a bypass flow 4.

It follows from the above that the dilution ratio, in other words the ratio of the volume flow of sample gas stream 1 to the volume flow of diluting gas stream 2, can be adjusted by varying the cycle ratio at which mixing valve 30 is switched back and forth. Since control signals 26 required for this purpose are generated by central control device 24, adjustments can be made immediately in a simple fashion by evaluating detection signals 22, if detection signals 22 do not fall within the provided value range. By virtue of this simple measure, assurance is provided that the chemical sensors are always operated in a nominal measuring range by varying the dilution ratio. In particular, the concept allows continuous (dynamic) detection of the concentration of the substances, even if the measured values are subject to very strong fluctuations over time. Feedback may be used in connection with this process.

If, as in the present embodiment, the volume flows of sample gas stream 1 and diluting gas stream 2 match, a conversion can be made to the (true) concentration value in gaseous medium 100 directly from the cycle ratio and the concentration value of the substance determined in measured gas stream 3. If, for example, mixing valve 30 switches back and forth in a ratio of 1/10 second to 9/10 second between sample gas stream 1 and diluting gas stream 2, a measured gas stream 3 with a dilution ratio of 1 to 10 is produced. The concentration values detected by chemical sensors 20 thus need only be multiplied by a factor of 10 to determine the actual concentration. The effective measuring range in this case would be increased by a factor of 10.

Control device 20 can be programmed in such fashion for example that the cycle ratio is varied in preset stages whenever the current detection signal 22 threatens to depart from the specified value range. It is advantageous in this connection to double the time cycle ratio so that dilution steps take place in dual sequence.

It is also possible to change the dilution ratio continuously so that it is possible to keep the measured value always at a predetermined preset optimum value in order to correlate the actual (true) concentration of the substance exclusively with the (continuously changing) dilution ratio. However, comparatively high computer cost is required in order to take into account dead times in the gas path and the delay times of the sensors.

Figure 2:
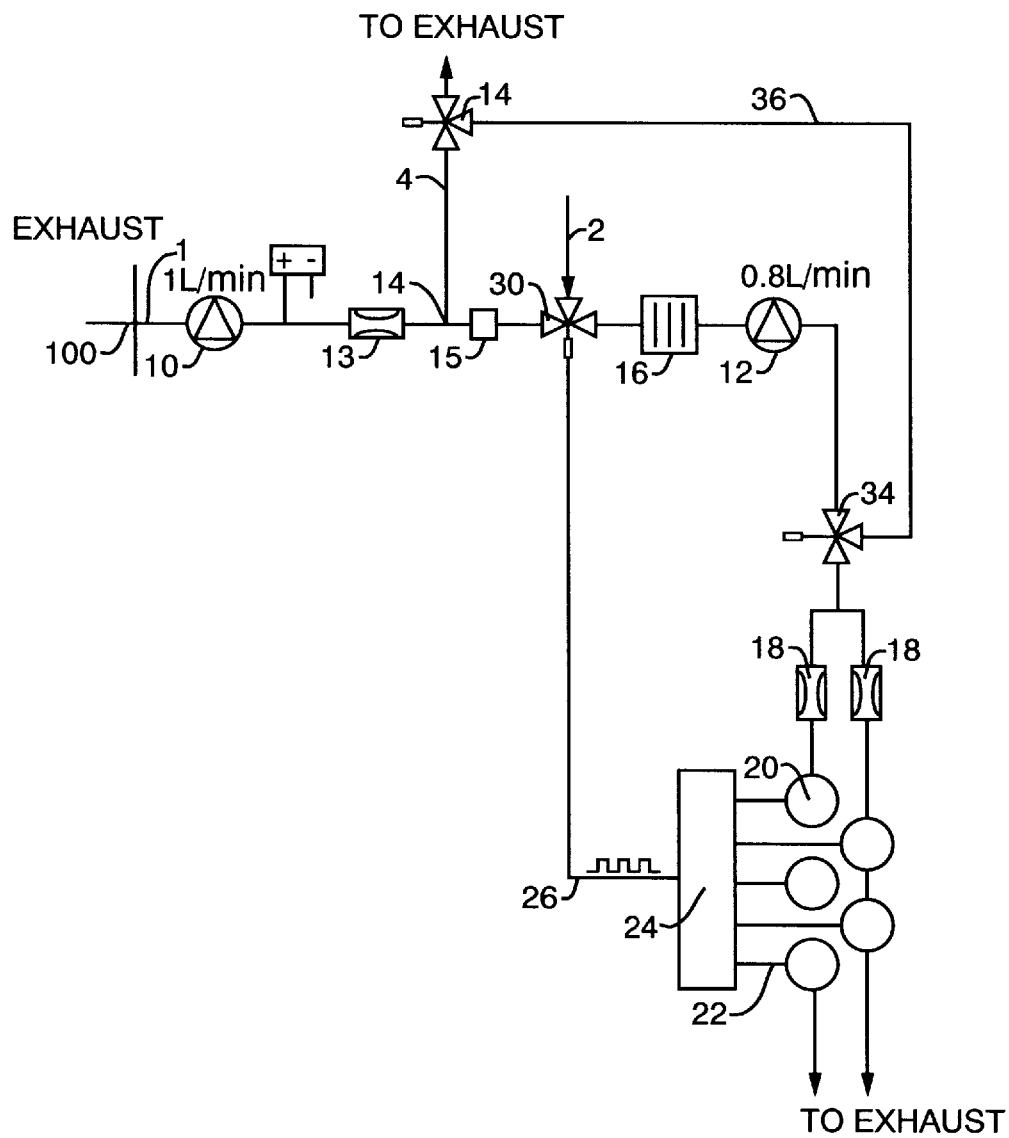
FIG. 2 is a schematic diagram of a device suitable for the purpose.

The configuration shown in FIG. 2 is based directly on the initial configuration according to FIG. 1. In addition to the large number of chemical sensors 20 that are divided into two parallel-connected pathways, there is also a bypass line 36 that bypasses all the components that dilute sample gas stream 1. Bypass line 36 branches off at branch 14 and is reconnected downstream from delivery pump 12 and upstream from capillaries 18. It thus permits so-called normal operation in which sample gas stream 1 is supplied to chemical sensors 20 without being diluted. In addition, a valve 32 is incorporated in bypass line 36, said valve being in the form of a 3/2-way valve and, depending on the switch position, allowing bypass-line 36 to be cleared or interrupting the latter and opening a path leading to the exhaust.

A valve 34 is also provided at the return point of bypass line 36 which alternately opens the path through bypass line 256 or the path for measured gas stream 3.

During normal operation, valves 32, 34 (as well as mixing valve 30) are in the resting position so that sample gas stream 1 takes the path through bypass line 36. Sample gas stream 1 is maintained by delivery pump 10. Delivery pump 12 is shut off.

For dilution operation, valves 32, 34 are opened (exposed to flow). Delivery pump 10 delivers sample gas into a prechamber 50 that acts as a buffer and from there through cycled mixing valve 30 into mixing chamber 16. Surplus sample gas can be blown out as before through branch 14 and open valve 32 to the exhaust. In addition, a diluting gas stream can be drawn in through cycled mixing valve 30 by delivery pump 12 and also supplied to mixing chamber 16. This mode of operation thus corresponds to the way in which the method was worked as described at the outset.

For the sake of completeness it should be pointed out that so-called normal operation in which sample gas stream 1 is not diluted is also basically possible with the configuration shown in FIG. 1. For this purpose, mixing valve 30 is constantly connected to the path of sample gas stream 1.

Because of its high measurement accuracy, the invention is suitable not only for measuring the composition of a highly concentrated exhaust by dilution, but can also be used for diluting highly concentrated test gas with a known composition in a specific fashion in order thereby to calibrate measuring equipment using a measurement series of different concentrations.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art which this invention pertains.

This application claims priority from German Application No. 196 43 981.7, the content of which is hereby incorporated by reference.

What I claim is:

1. A method for determining the concentration of a substance in a gaseous medium with a chemical sensor that has a nominal measuring range for the concentration of the substance, by removing a sample gas stream from the gaseous medium, mixing the sample gas stream with a diluting gas stream in a mixing device to form a measured gas stream in an adjustable dilution ratio, feeding the measured gas stream to the chemical sensor to generate a detection signal, and adjusting the dilution ratio in such fashion that the concentration of the substance detected by the chemical sensor is kept in the nominal measuring range, wherein, said sample gas stream and said diluting gas stream are each cycled alternately sequentially with definite volume flows to mixing device and that the dilution ratio is calculated on the basis of the cycle ratio.

2. The method according to claim 1, wherein the volume flows of said sample gas stream and said diluting gas stream have matching values.

3. The method according to claim 1, wherein the sample gas stream and diluting gas stream are supplied through a mixing valve located upstream from mixing device, said mixing valve being in the form of a 3/2-way valve, said mixing valve alternately opening a path for said sample gas stream and said diluting gas stream.

4. The method according to claim 3, wherein the mixing valve is actuated by a central control device that specifies the cycle ratio as a function of a detection signal.

5. The method according claim 1, wherein the dilution ratio is adjusted continuously.

6. The method according to claim 1, wherein an air stream obtained from the environment or a gas stream obtained from a pressurized tank is used as the diluting gas stream.

7. The method according claim 1, wherein the dilution ratio is initially set large enough to ensure that the test gas stream fed to the chemical sensor will be within a nominal measuring range of said sensor.

8. The method according to claim 1, wherein a plurality of chemical sensors for detecting a plurality of different substances are provided and the dilution ratio is regulated as a function of a detection signal of the chemical sensor sensing a largest deviation from its nominal measuring range.

9. The method according to claim 1, wherein the detection signal of the chemical sensor for a previous measurement is used to anticipate a subsequent detection signal and used to adjust the dilution ratio by gradient formation.

10. The method according to claim 1, wherein the detection signal of the chemical sensor is kept within a predetermined interval of the nominal measuring range by at least one of stepwise and continuous changes in the dilution ratio.

11. A chemical sensor, comprising:

a dilution device for diluting a sample gas stream with a diluting gas stream, in which said sample gas stream and said diluting gas stream are supplied cyclically and alternately through a 3/2-way mixing valve to a mixing device in which said sample gas stream and said diluting gas stream are mixed to form a measured gas stream, at least one chemical sensor for producing a detection signal indicative of a measured value of a concentration of a substance in measured gas stream, and a control device, to adjust a dilution ratio of said diluting gas stream to said sample gas stream as a function of the value of the detected concentration, by setting said cyclic supply so that the concentration of the substance in the measured gas stream is maintained within the nominal measuring range of chemical sensor.

12. The device according to claim 11, wherein the mixing device is designed as a mixing chamber with at least one of integral turbulence generators, nozzles, capillaries, and static mixers.

13. The device according to claim 11, wherein a switchable bypass is used to bypass the diluting device.

14. The device according to claim 11, wherein a prechamber is located upstream of the mixing valve.

15. The device according to claim 11, further comprising a delivery pump for the measured gas stream located downstream of the mixing chamber.

* * * * *